(12) United States Patent
Hagberg et al.

(10) Patent No.: US 9,340,552 B2
(45) Date of Patent: May 17, 2016

(54) METHOD OF MAKING ISOIDIDE

(71) Applicant: Stichting Dienst Landbouwkundig Onderzoek, PB Wageningen (NL)

(72) Inventors: Erik Hagberg, Decatur, IL (US); Kevin Martin, Mt. Zion, IL (US); Jerome Le Notre, BH Wageningen (NL); Daniel Stephan van Es, PB Wageningen (NL); Jacobus van Haveren, PB Wageningen (NL); Jan van Ee, PB Wageningen (NL)

(73) Assignee: Archer Daniels Midland Company, Decatur, IL (US)

( * ) Notice: Subject to any disclaimer, the term of this patent is extended or adjusted under 35 U.S.C. 154(b) by 217 days.

(21) Appl. No.: 14/375,230

(22) PCT Filed: Feb. 19, 2013

(86) PCT No.: PCT/NL2013/050105
§ 371 (c)(1),
(2) Date: Jul. 29, 2014

(87) PCT Pub. No.: WO2013/125950
PCT Pub. Date: Aug. 29, 2013

(65) Prior Publication Data
US 2014/0371472 A1    Dec. 18, 2014

(30) Foreign Application Priority Data

Feb. 20, 2012  (EP) ..................... 12156170

(51) Int. Cl.
*C07D 493/04*  (2006.01)
*B01J 23/42*   (2006.01)
*B01J 23/44*   (2006.01)
*B01J 23/46*   (2006.01)
*B01J 23/52*   (2006.01)
*B01J 23/755*  (2006.01)

(52) U.S. Cl.
CPC .............. *C07D 493/04* (2013.01); *B01J 23/42* (2013.01); *B01J 23/44* (2013.01); *B01J 23/462* (2013.01); *B01J 23/464* (2013.01); *B01J 23/52* (2013.01); *B01J 23/755* (2013.01)

(58) Field of Classification Search
CPC ...................................... C07D 493/04
USPC ........................................... 549/464
See application file for complete search history.

(56) References Cited

PUBLICATIONS

Ramstadius et al., Eu. J. Org. Chem. (2011) vol. 2011(23), pp. 4455-4459.*

* cited by examiner

*Primary Examiner* — Taofiq A Solola
(74) *Attorney, Agent, or Firm* — William B. Miller

(57) ABSTRACT

Disclosed is a process for the preparation of isoidide from isosorbide. An aqueous solution of isosorbide is subjected to epimerization in the presence of hydrogen under the influence of a catalyst comprising ruthenium on a support, preferably a carbon support. The process of the invention can be conducted using a relatively low hydrogen pressure, and leads to a desired distribution of epimers, favoring isoidide over isomannide and isosorbide.

9 Claims, No Drawings

METHOD OF MAKING ISOIDIDE

This application is a 35 U.S.C. §371 national phase entry of International Application No. PCT/NL2013/050105, filed Feb. 19, 2013, which claims priority from European Patent Application 12156170.8, filed Feb. 20, 2012.

FIELD OF THE INVENTION

The invention pertains to the synthesis of isoidide by epimerization from isosorbide.

BACKGROUND OF THE INVENTION

Isosorbide is a bicyclic diol, that is easily available from biological feedstock. Glucose can be hydrogenated to sorbitol. The latter, in turn, can be subjected to double dehydration so as to yield isosorbide. Its double hydroxyl function would make isosorbide of interest as a building block for polymerization. However, the making of polymers of suitable properties is hampered by the molecule's stereochemistry, since the two hydroxyl groups are directed to different sides of the molecule's plane. I.e., the up to now more easily obtainable isosorbide is unsymmetrical with one endo-hydroxyl group and one exo-hydroxyl group, resulting in asymmetrical reactivity and amorphous polymers (due to the lack of symmetry). Its epimer isomannide, which has two endo-hydroxyl groups, has proven to be unfavorable for polymerization due to low reactivity and low linearity. On the other hand, the epimer isoidide has two exo-hydroxyl groups, and has been viewed as far better suited for use as a building block for polymerization than either isosorbide or isomannide.

Isosorbide, which is the natural epimer, is capable of being converted into isomannide and isoidide, according to the following reaction scheme:

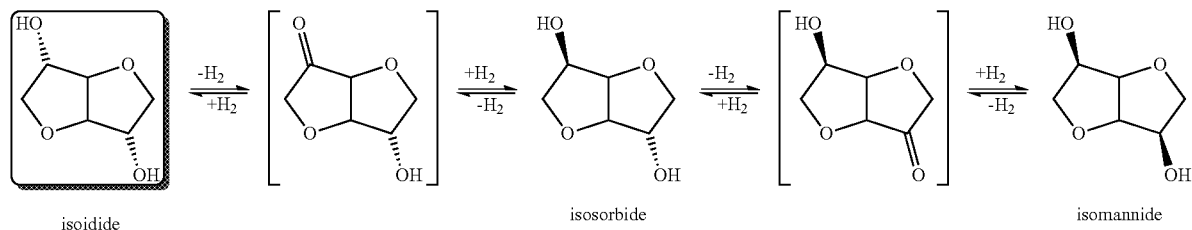

isoidide    isosorbide    isomannide

Isoidide as just mentioned is known as a building block for polymers. Examples include polyesters made by polycondensation of isoidide and a dicarboxylic acid or anhydride, and polycarbonates made by reaction with a bifunctional carboxyl compound such as phosgene. Isoidide is useful in other polymerizations wherein conventionally other diols are used. E.g., bisglycidyl ethers of isoidide can be used as a substitute for bisphenol-A in epoxy resins.

It is desired to be able to produce isoidide, whilst maintaining the original biomolecule as a feedstock. A suitable, economical method for commercial scale production, to date, does not exist.

As background art, reference is made to L. W. Wright, J. D. Brandner, *J. Org. Chem.*, 1964, 29 (10), pp 2979-2982. Herein it is disclosed to induce epimerization by means of Ni catalysis, using nickel supported on diatomaceous earth. The reaction is conducted under relatively severe conditions, such as a temperature of 220° C. to 240° C. at a pressure of 150 atmosphere. The reaction reaches a steady state after two hours, with an equilibrium mixture containing isoidide (57%), isosorbide (36%) and isomannide (7%). Comparable results were obtained when starting from isoidide car isomannide. Increasing the pH to 10-11 was found to have an accelerating effect, as well as increasing the temperature and nickel catalyst concentration. A similar disclosure is to be found in U.S. Pat. No. 3,023,223.

A desire in the art is to find an effective method to obtain isoidide in good yields, yet allowing more moderate reaction conditions. An additional challenge in providing such a method, is the need to avoid side-reactions, which lead to undesirable mass loss, e.g. as a result of hydrodeoxygenation.

Another background reference is C. Montassier et al., J. Mol. Catalysis, 70, 1991, p 65. This document generally concerns conversion of polyols into furanic derivatives using bimetallic catalysts. An incidental reference is made to epimerization of isosorbide into isoidide over an $SiO_2$ supported Ru catalyst. The disclosure does not, however, enable this epimerization. In fact, it can be derived from FIG. 6 in the reference, that after a reaction time of as long as six hours, a thermodynamic equilibrium has not been reached.

A further background reference is EP 1 647 540. Therein the synthesis is described of L-iditol starting from sorbitol. In a first step sorbitol is converted by fermentation into L-sorbose, which is subsequently hydrogenated into a mixture of D-sorbitol and L-iditol. This mixture is then converted into a mixture of L-iditol and L-sorbose. After separation from the L-sorbose, the L-iditol can be converted into isoidide. Thus, sorbitol is converted into isoidide in a four-step reaction, in a yield of about 50%. It would be desired to provide a more direct process, involving fewer steps, and providing a higher yield.

Hence, a need exists in the art to provide an effective method for the epimerization of isosorbide into isoidide, and catalysts therefore.

SUMMARY OF THE INVENTION

In order to better address the foregoing desire, the invention, in one aspect, provides a process for the preparation of isoidide from isosorbide, comprising subjecting an aqueous solution of isosorbide to epimerization in the presence of hydrogen under the influence of a catalyst comprising ruthenium on a support, at a starting pH of above 7.

In another aspect, the invention provides a process for the preparation of isoidide from isosorbide, comprising subjecting an aqueous solution of isosorbide to epimerization in the presence of hydrogen under the influence of a catalyst comprising ruthenium on a carbon support.

In yet another aspect, the invention provides the use of a catalyst comprising ruthenium on a carbon support, in the epimerization of isosorbide into isoidide.

In a still further aspect, the invention provides a process for the preparation of isoidide from glucose, the process comprising the steps of
(a) subjecting glucose to hydrogenation so as to form sorbitol;
(b) subjecting the sorbitol to dehydration so as to form isosorbide;
(c) subjecting isosorbide to catalyzed epimerization into isoidide, using a catalyst comprising ruthenium on a carbon support.

DETAILED DESCRIPTION OF THE INVENTION

In a broad sense, the invention is based on the discovery how to perform the epimerization of isosorbide into isoidide in such a way as to obtain a thermodynamic equilibrium and, particularly, in such a way as to avoid mass loss as a result of hydrodeoxygenation. This is believed to be accomplished by the selection of ruthenium as a catalytically active transition metal, on a support, in conjunction with the process condition of a starting pH of above 7, preferably of from 8 to 10. The starting pH refers to the pH of the aqueous solution of isosorbide.

It has been found that this catalyst serves to bring about the epimerization of isosorbide into isoidide in an efficient manner, under relatively mild conditions. In this respect, ruthenium acts more favorably than other metal catalysts, such as gold, platinum, palladium, and rhodium.

In investigating the catalysts, a particularly beneficial catalyst, also operable at below pH7, was found to comprise ruthenium on carbon as a support. Also, a carbon supported ruthenium catalyst acts more favorably in the epimerization of isosorbide, than other supports, e.g., $Al_2O_3$. The catalytically active metal preferably consists essentially of ruthenium, and the support preferably consists essentially of carbon.

In order to conduct the epimerization, isosorbide is provided in the form of an aqueous solution. The concentration of isosorbide therein may widely vary. However, for the sake of process economics as well as results in terms of yield, it is preferred for the isosorbide concentration to be in a range of from 25% by weight to 75% by weight. More preferably, the isosorbide concentration is 30% to 60% by weight. The optimum concentration is believed to approximately 50% by weight.

The aqueous solution is subjected to an atmosphere comprising hydrogen. The hydrogen pressure can widely vary, e.g. of from 20 to 200 bar. However, it was found particularly effective to employ a relatively low pressure in the range of from 25 to 55 bar, and preferably about 40 bar. The ability to use such low hydrogen pressures, provides the process of the invention with great advantage as compared to the above/mentioned process of Wright and Brandner.

The aqueous solution is subjected to said hydrogen atmosphere whilst being under the influence of a catalyst. The catalyst used in the invention comprises ruthenium as a catalytically active metal, and a support.

The support can vary widely, including silica, alumina, titania, zirconia, and carbon. The carbon support is preferred, inter alia since it can be operated at a wider pH range than other supports.

The amount of ruthenium on carbon catalyst used can vary widely, and will generally be determined on the basis of the ruthenium content.

Calculated on the basis of a water paste comprising 50% of a 5% ruthenium on carbon catalyst, the catalyst concentration in the reactor, calculated as a weight percentage based on the aqueous solution of isosorbide, can range from as low as, e.g., 1% to as high as, e.g. 50%. However, for the sake of process economics as well as results in terms of yield and specificity, it is preferred for a 5% ruthenium catalyst to be employed in a concentration of from 2 to 20%, and more preferably about 4%. It will be understood that these percentages will hold, mutatis mutandis, for other water paste concentrations than 50%, and other catalyst loadings than 5%.

A typical range of ruthenium, vis-à-vis isosorbide is 0.01 mole % to 1 mole %, preferably 0.0 to 0.2 mole %, and more preferably 0.03 mole % to 0.15 mole %.

The skilled person will be aware of how to generally conduct the ruthenium catalyzed reaction. Background references in this respect include U.S. Pat. No. 6,177,598 and U.S. Pat. No. 6,570,043.

The ruthenium catalyst preferably comprises a carbon support. Different types of carbon support are applicable, e.g. activated carbon or carbon nanotubes. The activated carbon can be, e.g., 50-70% wetted powder. Typically preferred catalysts include commercial ruthenium on carbon catalysts ex BASF or Evonik (Strem Chemicals). A background reference on Ru/C catalysts is Sifontes Herrera et al, J. Chem Technol Biotechnol (2011), "Sugar hydrogenation over a Ru/C catalyst."

The epimerization reaction is conducted preferably at an elevated temperature, i.e. above 20° C., and preferably below 250°. A preferred temperature range is 200° to 240°, most preferably about 220° C. The duration of the reaction will, as the skilled person knows, generally be shorter at higher temperatures. The residence time in the reactor where the isosorbide solution is subjected to hydrogen under the influence of the catalyst, will generally range from 0.1 to 10 hours, preferably, 0.25 to 4 hours, and more preferably 1-2 hours.

It is preferred to adjust the pH of the aqueous solution of isosorbide. Although, for the sake of conducting the epimerization per se, the pH may widely vary, it has been found that unwanted side reactions, which lead to loss of matter as a result of the formation of volatiles, can be reduced considerably by adjusting the pH to a value of 8 to 10.

Considering that the invention provides an advantageous, economically attractive process for the production of isoidide, the invention also enables a suitable overall process for the synthesis of the desired monomer isoidide, from glucose obtainable as biological feedstock.

Thus, the invention also provides a process for the preparation of isoidide from glucose, the process comprising the steps of
(a) subjecting glucose to hydrogenation so as to form sorbitol;
(b) subjecting the sorbitol to dehydration so as to form isosorbide;
(c) subjecting isosorbide to catalyzed epimerization into isoidide, using a catalyst comprising ruthenium on a support, at a pH above 7; preferably at a pH of 8 to 10, and more preferably on a carbon support.

Since, generally, step (c) will result in an equilibrium mixture of isoidide with isosorbide and isomannide, step (c) is preferably followed by a step comprising the recovery of isosorbide by separation from said mixture.

It will be understood that step (c) is conducted in conformity with the process as described hereinbefore. The preceding steps can be conducted as known in the art. Reference is made, e.g., to the conversion of glucose to sorbitol, which can be done also using a ruthenium on carbon catalyst. See, inter alia, U.S. Pat. No. 6,177,598 and U.S. Pat. No. 6,570,043; K. van Gorp et al., *Catalysis Today*, Vol. 52 (1999), p 349-361; V. Sifontes Herrera et al., J. Chem. Technol Biotechnol (2011), Wiley Online Library DOI 10.1002/jctb.2565. For both the conversion to sorbitol and the epimerization of isoidide, the same or different Ru/C catalysts can be used.

From the equilibrium mixture obtained in step (c), the isoidide can be recovered by separation methods known to the skilled person, such as by chromatographic techniques, selective crystallization or distillation. The latter can be conducted, e.g. as disclosed by Wright et al. *J. Org. Chem.*, 1964, 29 (10), pp 2979-2982, mentioned above.

The invention will hereinafter be illustrated with reference to the following non-limiting examples. Herein isosorbide was obtained from commercial sources.

Example 1

In a typical experiment the isosorbide solution in water was prepared by adjusting the pH using sodium hydroxide, and degassed with nitrogen by bubbling gas into the solution for 1 hour. The heterogeneous catalyst was weighed in air, placed in a glass liner with the stirring bar, and the liner was introduced into the reactor and the atmosphere was purged twice with nitrogen. The substrate solution was then added via syringe and the reactor was closed and purged 3 times with nitrogen. After purging of the gas lines, hydrogen was used to purge the reactor (3 times). The desired hydrogen pressure was then applied, stirring was started and heating began (typically heating was achieved in 25 minutes). The reaction time started when the desired temperature was reached.

After reaction, the reactor was allowed to cool down to room temperature and the excess gas pressure was released. The crude solution was filtered twice using two microfilters (Millipore, 0.45 μm then 0.20 μm), pH was measured, and the crude reaction mixture was dried in an oven overnight (T=60° C.). The crude syrup was then dried further in a dessicator under high vacuum for ca. 5 hours before analysis.

Experiments 1-12 are outlined in Table 1 below.

The first set of reactions (code 1 to 6) was performed using 1.1 g of isosorbide in 30 mL of water with 10 to 20 wt % of a 5% Ru/C catalyst at 50° C. for 4 to 24 hours. The crude mixtures were analyzed by $^1$H NMR is $D_2O$ after drying of an aliquot of the solution. No epimerization was observed and only isosorbide was recovered.

Reactions 7 to 10 were used to study the influence of temperature on the reaction and due to the closed system of the reactors, the initial pressure of hydrogen increased from 1 bar at room temperature to 24.5 bar at 220° C. for reaction 10. NMR analysis showed no conversion.

For reaction 11 and 12, the initial hydrogen pressure at room temperature was set at 30.0 bar and 54.5 bar, respectively. The internal pressure increased to 47.0 bar for reaction 11 and to 81.1 bar for reaction 12 at 220° C. Aliquots of the crude reactions mixtures were analyzed with NMR, which showed that for both reactions the epimerization of isosorbide had occurred, and the ratios observed between the three isomers indicates that the thermodynamic equilibrium had been reached within the reaction time of 3 h.

Example 2

As compared to Example 1, a number of reaction conditions were varied. First the substrate concentration was increased to 33 wt/wt %, and the catalyst loading was decreased from 20 wt % to 4 wt % (Table 2). The reactions were performed at 220° C. for 2 hours using different hydrogen pressures.

TABLE 2

Epimerization reactions at 33 wt/wt % isosorbide loading (5 g in 10 mL $H_2O$).

| Reaction Code | Catalyst | Loading (*) | $P(H_2)$ at r.t. (bar) | T (° C.) | P(reactor) at T° C. (bar) | Reaction Time (h) | Results IS/II/IM |
|---|---|---|---|---|---|---|---|
| 15 | 5% Ru/C (Strem) | 4 wt % | 10.3 | 220 | 23.1 | 2 | 95/4/1 |
| 16 | 5% Ru/C (Strem) | 4 wt % | 19.8 | 220 | 30.3 | 2 | 79/16/5 |
| 17 | 5% Ru/C (Strem) | 4 wt % | 30.1 | 220 | 44.8 | 2 | 56/37/7 |
| 18 | 5% Ru/C (Strem) | 4 wt % | 39.9 | 220 | 58.4 | 2 | 43/48/9 |

(*) A loading of 4 wt % corresponds to 4 wt % of the 50% water paste of 5% ruthenium on carbon, which is 0.001 wt % of ruthenium based on isosorbide, or 0.144 mol % of ruthenium.

TABLE 1

Epimerization reactions at 3.5 wt/wt % isosorbide loading (1.1 g in 10 mL $H_2O$).

| Reaction Code | Catalyst | Catalyst loading | $P(H_2)$ at r.t. (bar) | T (° C.) | P(reactor) at T° C. (bar) | Reaction Time (h) | Results IS/II/IM |
|---|---|---|---|---|---|---|---|
| 1 to 6 | 5% Ru/C (Strem) | 10-20 wt % | 1 | 50 | 1.4 | 4-24 | 100/0/0 |
| 7 to 10 | 5% Ru/C (Strem) | 20 wt % | 1 | 100-220 | 2.4-24.5 | 3 | 100/0/0 |
| 11 | 5% Ru/C (Strem) | 20 wt % | 30 | 220 | 47.0 | 3 | 35/60/5 |
| 12 | 5% Ru/C (Strem) | 20 wt % | 54.5 | 220 | 81.1 | 3 | 35/60/5 |

Example 3

A further set of experiments was performed to evaluate a) the effect of increasing the substrate concentration to 50 wt/wt % isosorbide in water to obtain a good comparison with U.S. Pat. No. 3,023,223, and b) the influence of the support material. All reactions were performed at catalyst loading of 4 wt %, at 220° C. with a reaction time of 4 hours. The hydrogen pressure was set at 40 bar at room temperature and reached approx. 58 bar at the reaction temperature.

TABLE 3

Epimerization reactions at 50 wt/wt % isosorbide loading (10 g in 10 mL $H_2O$).

| Reaction Code | Catalyst | Loading | T (° C.) | P(reactor) at T° C. (bar) | Reaction Time (h) | Results IS/II/IM |
|---|---|---|---|---|---|---|
| 19 | 5% Ru/C (Strem) | 4 wt % | 220 | 58.4 | 4 | 70/24/6 |
| 20 | 5% Ru/$Al_2O_3$ (Strem) | 4 wt % | 220 | 58.0 | 4 | 91/6/3 |
| 21 | 5% Ru/C (reduced, 50% water paste, BASF, Escat 4401) | 4 wt % | 220 | 58.3 | 4 | 36/58/6 |
| 22 | 5% Ru/C (58% water paste, Evonik) | 4 wt % | 220 | 57.0 | 4 | 38/55/6 |

Example 4

A next set of experiments was performed by tuning the initial pH (Table 4, 5, and 6). For all reactions the substrate concentration was fixed at 50 wt/wt % isosorbide (10 g) in water, the catalyst used was the 5% Ru/C (Escat 4401), the temperature was set at 220° C. and hydrogen pressure was tuned at approx. 40 bar at room temperature leading to a total pressure of approx. 60 bar at 220° C.

It is important to notice that the reaction time relates to the time that the reaction mixture is maintained at the experiment temperature, therefore this time is not taking into account the heating time (approx. 30 min in all cases), and the cooling time back to room temperature (approx. 2 hours) The reactions were magnetically stirred and the stirring (1000 rpm) started after the pressurization of the reactors and before the heating started to avoid overshooting of the temperature.

TABLE 4

Epimerization reactions at 50 wt/wt % isosorbide loading (10 g in 10 mL $H_2O$), 5% Ru/C (Escat 4401), 40 bar $H_2$ (initial pressure), 220° C.

| Reaction Code | Catalyst Loading | Initial pH | Reaction Time (h) | pH after reaction | Mass loss | Results IS/II/IM |
|---|---|---|---|---|---|---|
| 30* | 4 wt % | 8.0 | 4 | 8.0 | — | — |
| 36 | None | 8.0 | 2 | 8.0 | 0% | 100/0/0 |
| 21 | 4 wt % | 7.0 | 4 | nd | 25% | 36/58/6 |
| 24 | 4 wt % | 8.0 | 4 | 5.0 | 10.1% | 38/56/6 |
| 25 | 4 wt % | 9.0 | 4 | 5.5 | 8.1% | 38/56/6 |
| 26 | 4 wt % | 10.0 | 4 | 6.5 | 6.4% | 39/55/6 |
| 33 | 4 wt % | 11.0 | 4 | 8.5 | 2% | 100/0/0 |
| 54 | 4 wt % | 7.0 | 24 | 3.5 | 38% | 41/50/9 |

*Reaction without substrate.

TABLE 5

Epimerization reactions at 50 wt/wt % isosorbide loading (10 g in 10 mL $H_2O$), 4 wt % of 5% Ru/C (Escat 4401), 40 bar $H_2$ (initial pressure), 220° C., pH 10.0.

| Reaction Code | Reaction Time (h) | pH after reaction | Mass loss | Results IS/II/IM |
|---|---|---|---|---|
| 28 | 1 | 9.5 | 0% | 69/25/6 |
| 27 | 2 | 8.0 | 4.2% | 54/39/7 |
| 26 | 4 | 6.5 | 6.4% | 39/55/6 |

TABLE 6

Epimerization reactions at 50 wt/wt % isosorbide loading (10 g in 10 mL $H_2O$), 4 wt % of 5% Ru/C (Escat 4401), 40 bar $H_2$ (initial pressure), 220° C., pH 8.0.

| Reaction Code | Reaction Time (h) | pH after reaction | Mass loss | Results IS/II/IM |
|---|---|---|---|---|
| 43 | 0.25 | 8.0 | 0% | 46/46/8 |
| 47 | 0.5 | 7.5 | 0% | 44/49/7 |
| 37, 42 | 1 | 7.0 | 2.7% | 34/58/8 |
| 29 | 2 | 5.5 | 5.8% | 36/58/6 |
| 24 | 4 | 5.0 | 10.1% | 38/56/6 |

Example 5

The effect of the catalyst loading on the reaction rate was studied next (Table 7).

TABLE 7

Ru/C catalyst loading screening.

| Reaction Code | Ru/C catalyst Loading | Mol % Ru (based in IS) | Reaction Time (h) | pH after reaction | Mass loss | Results IS/II/IM |
|---|---|---|---|---|---|---|
| 37, 42 | 4 wt % | 0.144 | 1 | 7.0 | 2.7% | 34/58/8 |
| 49 | 2 wt % | 0.072 | 1 | 7.0 | 1.9% | 42/50/8 |
| 56 | 2 wt % | 0.072 | 2 | 5.5 | 6.7% | 36/57/7 |
| 50 | 1 wt % | 0.036 | 1 | 7.0 | 0% | 51/41/8 |
| 55 | 1 wt % | 0.036 | 2 | 6.5 | 1.3% | 38/55/7 |
| 41 | 0.1 wt % | 0.004 | 1 | 7.5 | 0% | 100/0/0 |

Reaction conditions: 5% Ru/C (reduced, 50% water paste, Escat 4401), 50 wt/wt % isosorbide (10 g) in water (pH 8), 40 bar $H_2$ at R.T., 220° C.

By decreasing the catalyst loading from 4 wt % to 2 wt % the thermodynamic equilibrium was not reached after 1 hour reaction (reaction 49) but was achieved after 2 hours, however with a mass loss of 6.7% (reaction 56). Using 1 wt % of catalyst the results appeared similar with the thermodynamic equilibrium reached after 2 hours and a mass loss reduced to 1.3% (reaction 50, 55). Lower catalyst loading showed no activity (reaction 41).

Example 6

Different metal catalysts on different supports were tested using the standard reaction conditions and the results were compared to Ru/C (Table 8).

TABLE 8

Catalysts screening.

| Reaction Code | Catalyst Loading | Mol % Metal (based in IS) | Reaction Time (h) | pH after reaction | Mass loss | Results IS/II/IM |
|---|---|---|---|---|---|---|
| 37, 42 | 4 wt % of 5% Ru/C (reduced, 50% water paste, Escat 4401) | 0.144 | 1 | 7.0 | 2.7% | 34/58/8 |
| 51 | 4 wt % of 5% Ru/Al$_2$O$_3$ (Strem) | 0.289 | 1 | 6.0 | 5.1% | 77/18/5 |
| 44 | 4 wt % of 5% Pd/C (reduced, 50% water paste, Escat 1421) | 0.137 | 1 | 8.0 | 0% | 100/0/0 |
| 45 | 4 wt % of 5% Pt/C (reduced, 50% water paste, Escat 2421) | 0.075 | 1 | 7.0 | 0%(*) | 100/0/0 |
| 48 | 4 wt % of 5% Rh/C (reduced, wet, Degussa, G106B/W) | 0.284 | 1 | 5.0 | 6.7% | 100/0/0 |
| 53 | 4 wt % of 5% Au/C (52% water paste, Evonik) | 0.077 | 1 | 8.0 | 8.5% | 100/0/0 |
| 46 | 1.25 wt % of 64% Ni/SiO$_2$ (BASF, Ni-5249P) | 2.0 | 1 | 6.5 | 0% | 54/38/8 |
| 57 | 1.25 wt % of 64% Ni/SiO$_2$ (BASF, Ni-5249P) | 2.0 | 2 | 7.0 | 0%(*) | 44/49/7 |
| 58 | 1.25 wt % of 64% Ni/SiO$_2$ (BASF, Ni-5249P) | 2.0 | 4 | 6.0 | 0%(*) | 41/53/6 |
| 59 | 1 wt % of 20% Pd(OH)$_2$/C (Pearlman's catalyst, 50% water paste, unreduced, Escat 1951) | 0.103 | 1 | 7.5 | 0% | 100/0/0 |

Reaction conditions: 50 wt/wt % isosorbide (10 g) in water (pH 8), 40 bar H$_2$ at r.t., 220° C.
(*)Traces of HDO products.

Example 7

A series of reactions was performed at different temperatures (Table 10).

TABLE 10

Epimerization reactions at 50 wt/wt % isosorbide (10 g) in water (pH 8), 1 wt % of 5% Ru/C (reduced, 50% water paste, Escat 4401), 40 bar of H$_2$ (initial pressure).

| Reaction Code | Temperature (° C.) | Reaction Time (h) | pH after reaction | Mass loss | Results IS/II/IM |
|---|---|---|---|---|---|
| 71 | 160 | 2 | 7.5 | 1.5% | 95/4/1 |
| 70 | 180 | 2 | 7.5 | 3.1% | 85/12/3 |
| 69 | 200 | 2 | 7.5 | 3.0% | 63/31/6 |
| 68 | 220 | 2 | 7.0 | 4.2% | 37/56/7 |
| 67 | 240 | 2 | 6.0 | 5.0% | 39/54/7 |
| 66 | 220 | 22 | 3.5 | 16.3% | 36/58/6 |

Example 8

A large scale reaction was performed in a 600 mL Parr reactor with 200 g of isosorbide (1.37 mol) in 200 mL of water at pH 8 (mechanical stirrer at 500 rpm). Ruthenium (5%) on carbon (reduced, 50% water paste, Escat 4401) was used at a loading of 1 wt %. The reaction vessel was pressurized with 40 bar of hydrogen and heated at 220° C. for 2 hours. Aliquots of the reaction mixture were taken during the heating time and along the reaction. Those aliquots were obtained by manually opening the deep tube tab, then by flushing the tube (2-3 mL), and finally by collecting the sample (2 mL), which was analyzed following the standard procedure (Table 11).

TABLE 11

Epimerization reactions at 50 wt/wt % isosorbide (200 g) in water (pH 8), with 1 wt % of 5% Ru/C (Escat 4401), 40 bar H$_2$ (initial pressure).

| Temperature (° C.) | Time (min) | P(reactor) at T ° C. | pH | Results IS/II/IM |
|---|---|---|---|---|
| 160 | | | 8.0 | 100/0/0 |
| 180 | | | 8.0 | 100/0/0 |
| 200 | | | 8.0 | 97/2/1 |
| 220* | 0 | 61 | 8.0 | 93/6/1 |
| 220 | 15 | | 7.5 | 90/7/3 |
| 220 | 30 | 58 | 7.0 | 74/21/5 |
| 220 | 60 | 54 | 6.5 | 65/28/7 |
| 220 | 80 | 50 | 6.0 | 59/34/7 |
| 220 | 120 | 48 | 5.5 | 52/40/8 |
| r.t. | | | 5.0 | 49/43/8 |

The heating time took approximately 30 min and after 2 h reaction, the reactor was removed from the heating apparatus and let to cool down to room temperature in 2 hours.
*Overshoot to 236° C.

Example 9

Separation of Isosorbide, Isoidide, and Isomannide by Distillation

The purification of the crude mixture comprising isosorbide, isoidide, and isomannide was conducted following the procedure described by Wright et al., who performed the separation of the three isomers by distillation under vacuum.

Starting from 145 g of a 49/43/8 isosorbide/isoidide/isomannide mixture, we used a standard glassware set-up with a vacuum-jacketed Vigreux column (L=20 cm; ID=2 cm) to separate the three isomers. The vacuum was first tuned to 2 mbar and the oil bath heating was started. Three cuts were performed according to the vapors temperatures:

- 128-137° C. (2 mbar): 12.5 g of a colorless syrup was collected and analysis showed isomannide as the main product with traces of "non-volatiles" HDO products (diols) and traces of isosorbide;
- 151-156° C. (2 mbar) then 156-171° C. (2 mbar): 97.0 g of a colorless syrup containing mainly isosorbide (80%) with isoidide (20%);
- 111-113° C. (10-2 mbar): 28.9 g of a white solid analyzed as pure isoidide.

During the distillation of the third cut, the pure isoidide crystallized in the collecting part of the distillation set-up and was warmed-up carefully with a heatgun to allow its collection in the flask. Isoidide was isolated in an amount of 28.9 g, corresponding to a yield for the distillation step of 46%.

The invention claimed is:

1. A process for the preparation of a thermodynamic equilibrium concentration of isoidide from isosorbide, comprising subjecting an aqueous solution of isosorbide to epimerization in the presence of hydrogen under the influence of a catalyst comprising ruthenium on a support, at a starting pH of above 7, for a sufficient time and under other conditions suitable for obtaining a thermodynamic equilibrium condition.

2. A process for the preparation of a thermodynamic equilibrium concentration of isoidide from isosorbide, comprising subjecting an aqueous solution of isosorbide to epimerization in the presence of hydrogen under the influence of a catalyst comprising ruthenium on a carbon support, for a sufficient time and under other conditions suitable for obtaining a thermodynamic equilibrium condition.

3. A process according to claim 1 or claim 2, wherein the isosorbide concentration is in a range of from 25% by weight to 75% by weight.

4. A process according to claim 1 or claim 2, wherein the hydrogen is provided under a pressure of 25 to 55 bar.

5. A process according to claim 1 or claim 2, wherein the catalyst is loaded with 1% to 10% by weight of ruthenium, based on the total weight of the catalyst.

6. A process according to claim 1 or claim 2, wherein the catalyst is present in such an amount as to provide a mole percentage of ruthenium calculated in respect of isosorbide in a range of from 0.1 mole % to 0.2 mole %.

7. A process according to claim 1 or claim 2, wherein the epimerization reaction is conducted at a temperature in the range of from 200° C. to 240° C.

8. A process according to claim 1 or claim 2, wherein the epimerization reaction is conducted for a duration of 1-2 hours.

9. A process according to claim 1 or claim 2, wherein the pH of the aqueous isoidide solution is in the range of from 8-10.

* * * * *